United States Patent
Masumura

(10) Patent No.: US 8,817,255 B2
(45) Date of Patent: Aug. 26, 2014

(54) APPARATUS AND METHOD FOR IRRADIATING A SCATTERING MEDIUM

(75) Inventor: Takahiro Masumura, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 191 days.

(21) Appl. No.: 13/327,627

(22) Filed: Dec. 15, 2011

(65) Prior Publication Data
US 2012/0182558 A1    Jul. 19, 2012

Related U.S. Application Data

(60) Provisional application No. 61/424,535, filed on Dec. 17, 2010.

(51) Int. Cl.
*G01N 21/00* (2006.01)
*G01B 11/02* (2006.01)

(52) U.S. Cl.
USPC .......................................................... 356/338

(58) Field of Classification Search
USPC ............................ 356/337, 338, 432, 436, 441
See application file for complete search history.

(56) References Cited

U.S. PATENT DOCUMENTS

| | | | |
|---|---|---|---|
| 4,385,634 A | 5/1983 | Bowen | |
| 5,424,843 A | 6/1995 | Tromberg et al. | |
| 5,441,054 A | 8/1995 | Tsuchiya | |
| 5,477,051 A | 12/1995 | Tsuchiya | |
| 5,517,987 A | 5/1996 | Tsuchiya | |
| 5,587,832 A | 12/1996 | Krause | |
| 5,713,356 A | 2/1998 | Kruger | |
| 5,840,023 A | 11/1998 | Oraevsky et al. | |
| 6,721,094 B1 * | 4/2004 | Sinclair et al. | 359/386 |
| 6,738,653 B1 | 5/2004 | Sfez et al. | |
| 2008/0037367 A1 | 2/2008 | Gross et al. | |
| 2009/0009834 A1 | 1/2009 | Yaqoob et al. | |
| 2011/0109962 A1 * | 5/2011 | Cui et al. | 359/385 |

FOREIGN PATENT DOCUMENTS

WO    2010/084478 A2    7/2010

OTHER PUBLICATIONS

Vellekoop, et al., "Focusing coherent light through opaque strongly scattering media", Optics Letters 32(16), 2309-2311 (2007), The Netherlands.
Vellekoop, et al. "Demixing light paths inside disordered metamaterials" Optics Express 16, 67-80 (2008), The Netherlands.
Cui et al., Implementation of a digital optical phase conjugation system and its application to study the robustness of turbidity suppression by phase conjugation, Optics Express, Feb. 15, 2010, pp. 3444-3455, vol. 18, No. 4.

* cited by examiner

*Primary Examiner* — Michael A Lyons
(74) *Attorney, Agent, or Firm* — Canon USA Inc IP Division

(57) ABSTRACT

An apparatus includes a light source configured to emit an electromagnetic wave; a spatial light modulator configured to modulate a wavefront of the electromagnetic wave to irradiate a sample; a plate with an aperture; a lens unit configured to set a focal point in the sample; a detector configured to detect light coming from the focal point of the sample through the aperture; and a controller configured to control the spatial light modulator based on the detected light by the detector.

16 Claims, 4 Drawing Sheets

APPARATUS AND METHOD FOR IRRADIATING A SCATTERING MEDIUM

CROSS REFERENCE TO RELATED APPLICATION

This application claims priority to U.S. provisional application No. 61/424,535 filed Dec. 17, 2010 entitled IRRADIATION METHOD WITH CONFOCAL SYSTEM FOR FOCUSING LIGHT INSIDE A SCATTERING MEDIUM, the entire contents for which are hereby incorporated by reference herein.

BACKGROUND OF THE INVENTION

1. Field of the Invention

The present invention relates to an apparatus and a method for irradiating a scattering medium.

2. Description of the Related Art

Vellekoop et al. demonstrated that focusing light through scattering medium is possible by controlling the incident wavefront with spatial light modulator(SLM) and their phase optimization algorithm (Vellekoop, I. et al, Opt. Lett. 32(16), 2309-2311 (2007)). They infer an optimal incident wavefront in such a way that the target intensity monitored by a CCD becomes highest at given segment (pixel) on the SLM by cycling its phase from 0 to $2\pi$. Once they finished optimizing the wavefront, the incident light which has the optimized wavefront can focus light at a CCD plane.

Focusing light just after passing through a scattering medium is possible by controlling the wavefront of the incident light with the SLM. The position of the focus point obtained by this technique, however, is not inside the scattering medium but behind the medium where light is transmitted.

Vellekoop et al. further disclosed the way to focus light inside the scattering medium where a fluorescence probe lies (Vellekoop, I. et al, Opt. Express 16, 67-80 (2008)). The focused light intensity can be monitored by a CCD and control a SLM to optimize the incident wavefront for focusing. However, positions of fluorescence probes in a sample cannot be controlled.

SUMMARY OF THE INVENTION

According to an aspect of the present invention, an apparatus includes a light source configured to emit an electromagnetic wave; a spatial light modulator configured to modulate a wavefront of the electromagnetic wave to irradiate a sample; a plate with an aperture; a lens unit configured to set a focal point in the sample; a detector configured to detect light coming from the focal point of the sample through the aperture; and a controller configured to control the spatial light modulator based on the detected light by the detector.

According to another aspect of the present invention, an apparatus includes a light source configured to emit an electromagnetic wave to irradiate a sample; a beam splitter configured to split the electromagnetic wave into a reference beam and an object beam, the sample being irradiated by the object beam; a plate with an aperture; a lens unit configured to set a focal point in the sample; a detector configured to detect an interference pattern formed by the reference beam and a reflection beam coming from the focal point of the sample, through the aperture of the plate, in response to irradiation by the object beam; a spatial light modulator configured to modulate a wavefront of the electromagnetic wave; and a controller to control the spatial modulator based on the detected interference pattern so that the spatial light modulator forms a phase conjugate wave which travels to the focal point.

Further features of the present invention will become apparent from the following description of exemplary embodiments with reference to the attached drawings.

DESCRIPTION OF THE EMBODIMENTS

Embodiments according to the present invention will be described below with reference to the attached drawings.

Figure 1:
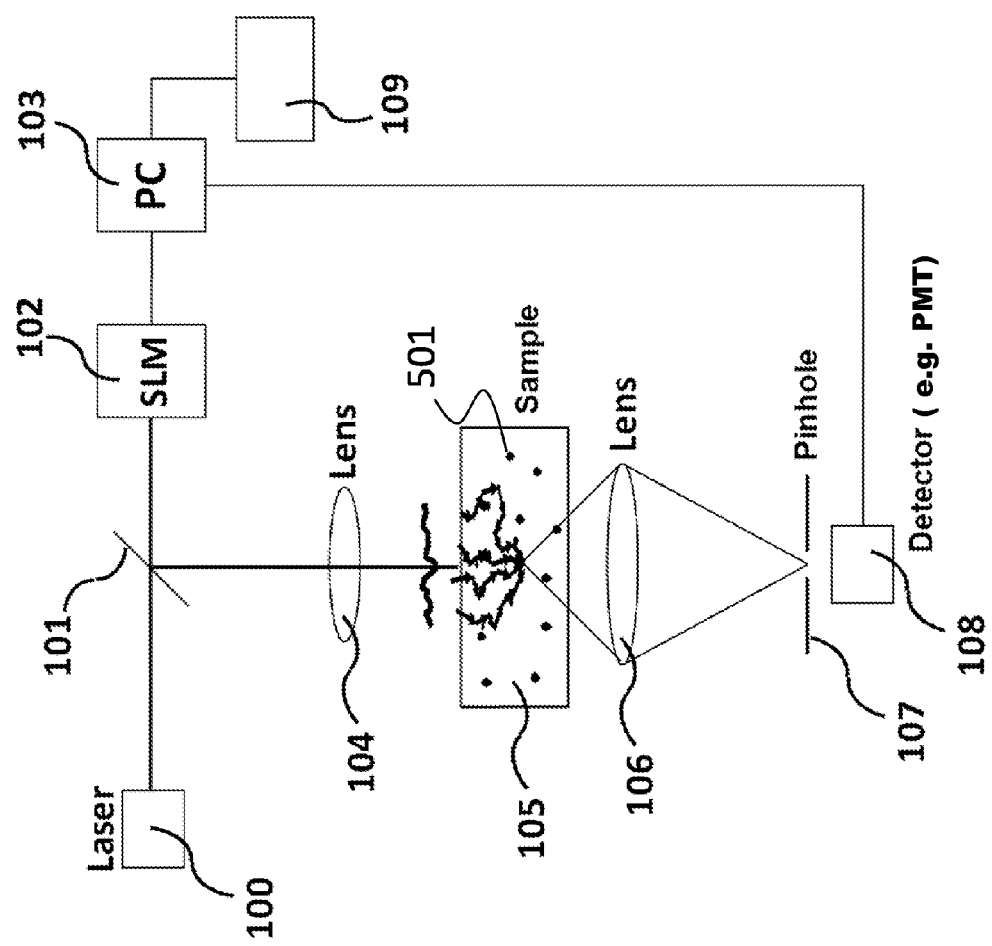
FIG. 1 illustrates an irradiating apparatus as a first embodiment.

FIG. 1 illustrates a diagram of an exemplary configuration of an irradiating apparatus as a first embodiment. A laser 100 emits light. The light can be a continuous-wave (CW) or pulsed light. The wavelength of the light can range from visible to near infrared light. For example, the wavelength can be selected from about 380 nm to about 2500 nm, such as from 400 nm to 1500 nm. The emitted light transmits through a mirror 101 and impinges onto a SLM (Spatial Light Modulator) 102, such as a liquid crystal on silicon (LCOS) or a digital micro-mirror device (DMD).

The SLM 102 controlled by a control unit 103 changes phases of a wavefront of the light according to an optimization algorithm performed by the control unit 103 and is described later. This spatially modulated wavefront is led to a sample 105 as a scattering medium through a lens system 104. The system has a confocal-based detection system and the control unit 103 may set a focal point of the confocal system including a lens unit 106 and a plate 107 with an aperture (pinhole). The sample 105 includes a scatterer 501. The confocal system including the lens unit 106 and the aperture may be movable to set the focal point in the sample, and/or the sample may be hold by a movable holder (not shown).

In the scattering medium 105, the light suffers scattering and some portion of the light may reach the local region where the confocal system is focused. The aperture of the plate 107 obstructs the light that is not coming from the focal point as a typical confocal system does and permits photons coming from the focal point to go through the aperture of the plate 107 to be detected by a photodetector 108, such as photomultiplier tube (PMT).

The detected light signal is originated from the local region where the confocal system 106 is focused. Therefore, it may be possible to monitor the light intensity at a specific position inside the scattering medium by the confocal system to optimize the incident wavefront to focus light inside the scattering medium. Here, the scattering medium 105 can be, for example, a biological tissue or any other turbid medium or disordered material.

Figure 2:
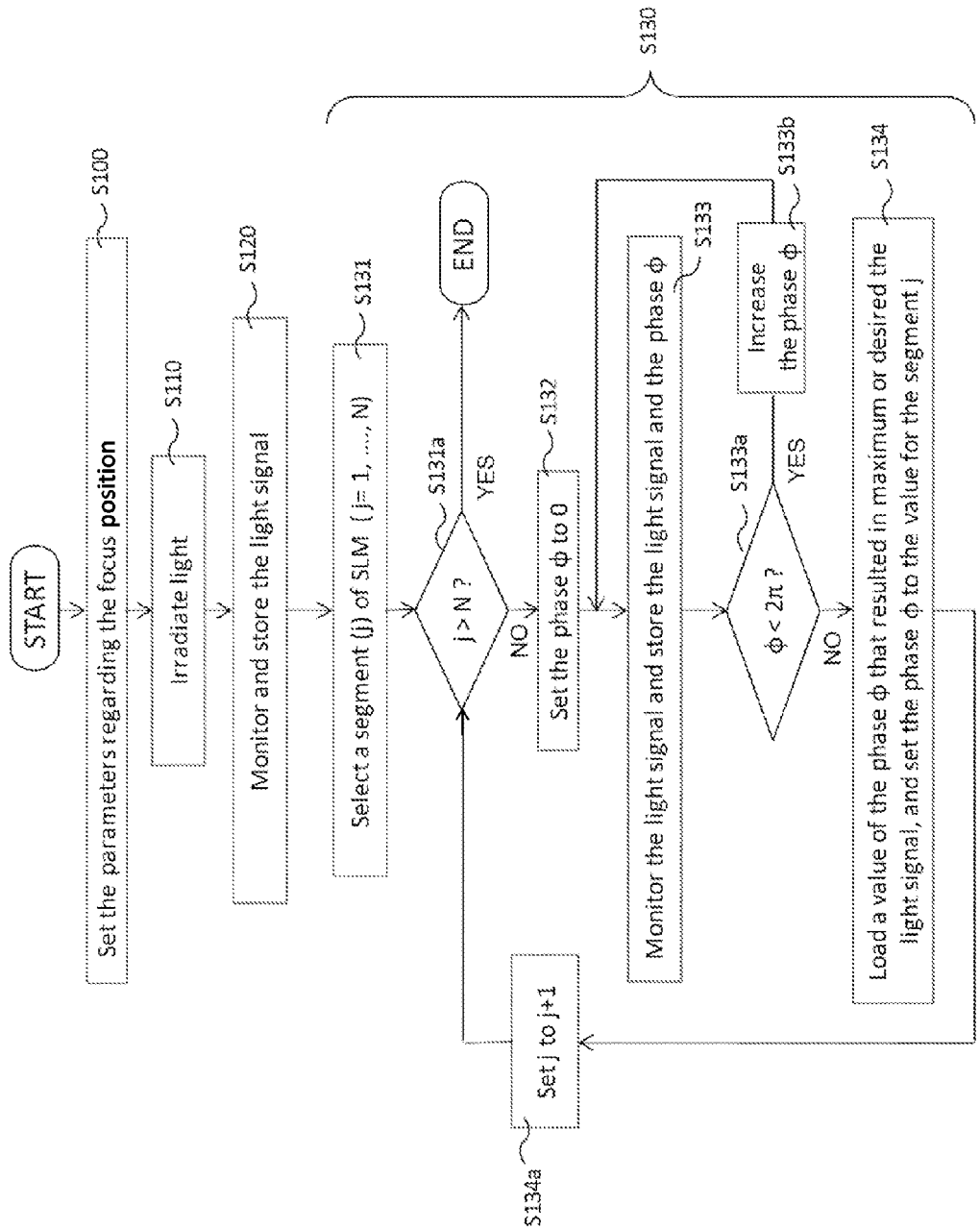
FIG. 2 illustrates an exemplary operation flow to optimize a wavefront.

FIG. 2 illustrates an exemplary operation flow of the first embodiment. At first, the parameter conditions regarding a focus position defined by the confocal system, such as the position or the size of the local region, is set at S100, and the light source 100 can emit light at S110.

The light signal originated from the local region can be selectively received by the detector 108 and monitored and stored in a memory. The monitoring and storing can be executed by the control unit 103 at S120.

After the control unit 103 has stored the information about the intensity of the light signal, the control unit 103 controls the SLM 102 and starts an optimization process at S130. The optimization process S130 consists of several sub-flows as described below.

At S131, one of the segments of the SLM 102 is controlled by the control unit 103 to change its phase of incoming light. Here, the segment of the SLM 102 may include a single pixel or a plurality of pixels of the SLM 102. The configuration of this segmentation may also be determined at 5100. At S131*a*, it is determined if processing has been performed for all of the segments. If processing has been performed for all of the segments (j>N is YES in S131*a*), processing of FIG. 2 ends. If processing has not been performed for all of the segments, at S132, the phase φ of the current segment j being processed is set to 0. The light signal for the segment at the currently set phase φ is monitored and stored with the phase φ at S133. At S133*a*, it is determined if all phases from 0 to 2π have been processed for the current segment j. If processing for all phases between 0 and 2π has not been performed for the current segment (phase φ<2π is YES in S133*a*), at S133*b*, the phase for the current segment is increased, for example, the phase can be continuously or discretely changed from 0 to 2π. After increasing the phase φ, processing returns to S133 where the light signal and the phase for the segment at the currently set phase φ is monitored and stored.

When processing for all phases between 0 and 2π has been performed for the current segment (phase φ<2π is NO), at S134, the control unit 103 picks up the phase that generated the largest light signal during the step S132 and S133, and assigns the phase at the segment j. Processing then moves to S134*a* to repeat the above described processing for the next segment j. This process is repeated until all of the segments on the SLM 102 are completed (segment j>N is YES in S131*a*). In S134, a value of the phase that resulted in maximum or specified light signal will be loaded, and the phase for the segment j is set to the value. According to FIG. 2, in the manner described above, each segment may be treated consecutively and independently. At the end of S130 (segment j>N is YES in S131*a*), the optimized phase distribution on the SLM 102 to be able to focus on the local region 108 can be created. In short, light with the optimized phase distribution can focus on the local region 108. After the optimized phase distribution has been obtained, a power of light with the optimized phase distribution, which is input into the medium as the sample for imaging, can be different from that of the initial light used in the optimization process. For this purpose, the light source can have a power controller to change the power of the light.

The local region in the scattering medium 105, where the confocal system is focused may be scanned in the scattering medium 105 to obtain three-dimensional image. The size of the focus point or pinholes size may be changeable. Furthermore, the above-described process may be performed using a plurality of desired wavelengths of the laser source 100 to obtain spectrum images and to extract functional information related to biochemical or metabolism for medical application.

An image generating process can follow the process. The control unit 103 may reconstruct three-dimensional image using the data obtained from the detector 108. The control unit can map the detected intensity in accordance with the position of the local region where the incident light focuses. The image can be displayed on a display device 109.

Here, although the system described above is transmittance geometry, this technique can be applicable to reflectance geometry as well.

By focusing light on the measurement region of the medium, it may be possible to enhance the measurement depth and SNR (Signal/Noise Ratio) of confocal based imaging or spectroscopy system such as confocal laser scanning microscopy. Especially it may be beneficial for the system which requires high energy to cause non-linear effect such as two-photon confocal or multi-photon confocal microscopy or confocal Raman microscopy.

After the optimized wavefront has been obtained, the focus position in the sample can be irradiated by the optimized wavefront, and then a signal reflected back from the sample or a signal generated in response to the irradiation can be detected for imaging of the sample.

Figure 3:
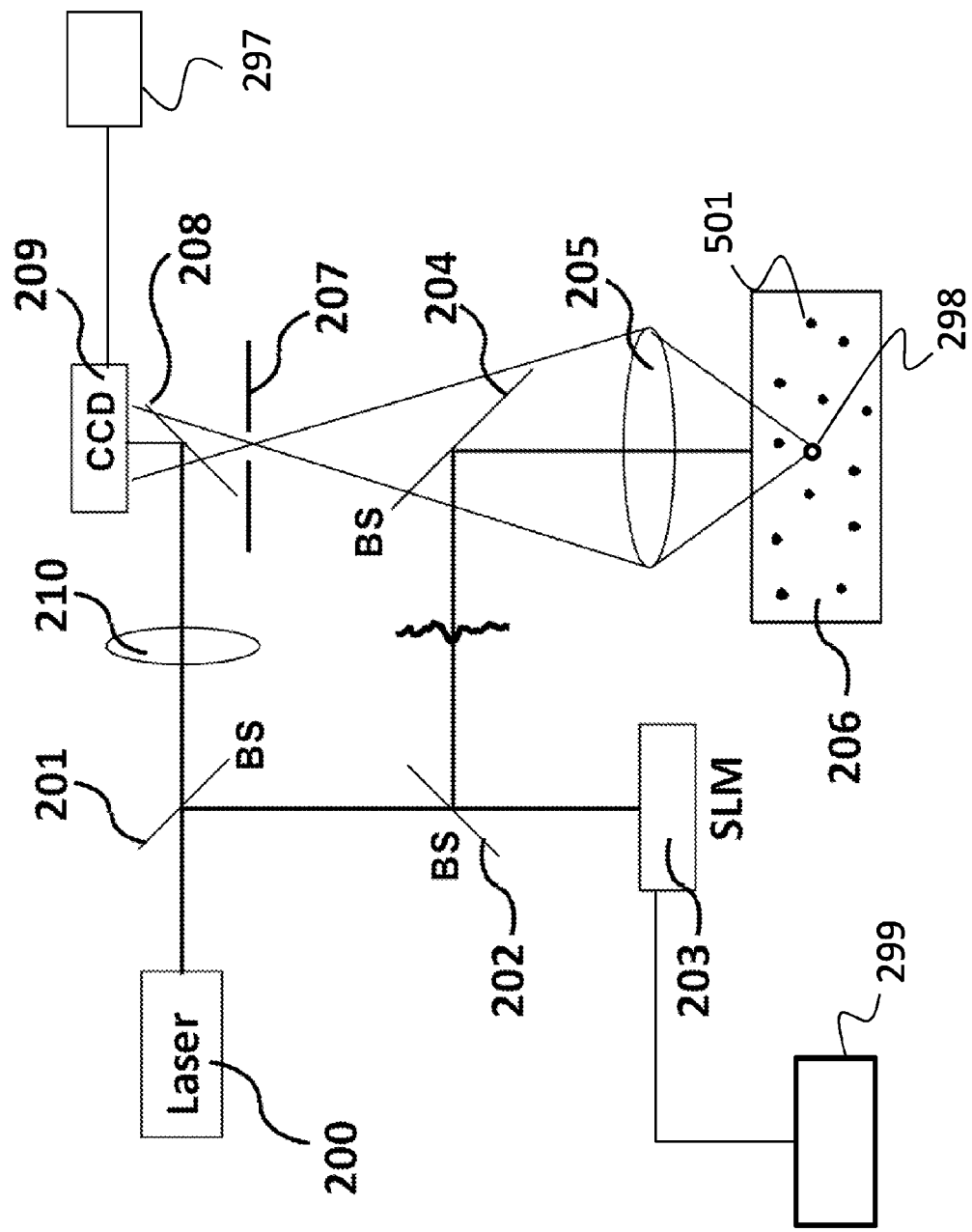
FIG. 3 illustrates another irradiating apparatus as a second embodiment.

FIG. 3 illustrates a diagram of a second exemplary configuration of a confocal imaging system with the irradiating apparatus, as a second embodiment. A laser 200 emits an initial light (e.g., CW light). The initial light can be split into an incident light and reference light by a beam splitter 201. The incident beam (object beam) impinges onto a SLM 203 via a beam splitter 202. The SLM 203 controlled by a control unit 299 changes phases of a wavefront of the incident beam according to a phase distribution obtained by a digital holography technique.

If the hologram data is not obtained in advance, to prepare the hologram data, the SLM 203 can be used as a mirror to input a plane wave into the medium 206, and then detect an interference pattern formed by the reference light and light coming from the focal point 298 of the medium 206. If the hologram data is obtained in advance, for example by using the first embodiment, the SLM 203 can be controlled according to the hologram data so that a phase conjugation wave is input into the medium 206.

The spatially modulated incident light is led to a scattering medium 206 through a beam splitter 204 and a lens unit 205. A focal point 298 is set inside the medium 206 by a confocal system including the lens unit 205 and an aperture of a plate 207 to detect light coming from the focal point 298 of the medium 206. The medium 206 contains a scatterer 501. As already described above, the aperture of the plate 207 (e.g., a plate with a pinhole) can reject photons coming from points other than the focus point 298. Photons coming from the focus point may go through the aperture of the plate 207 and a beam splitter 208, and impinges onto a detector comprising a CCD sensor 209. Here, a CMOS sensor or area sensors with an image intensifier, or EMCCD (Electron Multiplying CCD) are also applicable. The reference light is led to the CCD 209 through a lens 210 to create a hologram, which is based on interference between the reference light and the light reflected back from the focal point through the aperture of the plate 207, on the CCD 209. The hologram can be stored in a memory or a storage medium, such as a hard disk, as digital hologram.

The control unit 299 controls the SLM 203 based on the digital hologram, in order to generate a reconstructed light which may be equivalent to the phase conjugation (phase conjugate wave) by utilizing a digital holography technique. By using phase shifting holography technique, the phase and amplitude information of the detected light can be obtained. The control unit 299 sets the phase value of each pixel of the SLM 203 according to the phase distribution obtained by the digital hologram. At this time, the difference of the optical length between the CCD 209 and the SLM 203 or any other system error may be calibrated, and the phase values may be corrected. Alternatively, the CCD 209 and the SLM 203 may be arranged so that the optical length from the exit plane (or the set focal point) of the medium 206 to those devices is the same.

The SLM 203 modulates the phase of light emitted by the laser 200. This phase modulation develops a reconstructed light which may be equivalent to the phase conjugation and can retrace the trajectory back to the focal point 298 set by the confocal system.

The reconstructed light beam developed by the SLM 203 is configured to irradiate the medium 206. Because of the time-reversible nature, the phase conjugation can retrace its trajectory back to the focal point 298, the reconstructed light can focus to the local point. By focusing light on the local region, it may be possible to enhance the measurement depth or SNR of the confocal imaging system.

If the CCD 209 has a larger number of pixels compared to the SLM 203, the CCD 209 may perform binning so that the number of pixels between them is equal and those pixels are corresponding with each other.

With the generated phase conjugation wave, the focal point 205 in the medium 206 can be irradiated, and then a signal reflected back from the focal point 298 or a signal generated in response to the irradiation can be detected for imaging of the sample. Here, the power of the reconstructed light may be different from that of the initial light used in the recording process. For this purpose, the light source can have a power controller to change the power of the light.

Alternatively, instead of using digital holography technique, this embodiment can be achievable by using holographic material, such as photorefractive crystal or polymer to record the hologram. After recording the hologram in the holographic material, the phase conjugation may be generated by shining light from the opposite direction to the reference light. The generated phase conjugation may retrace to the focal point to increase the light intensity at specific point. The following reference is hereby incorporated by reference in its entirety as though fully and completely set forth herein: U.S. Patent Application Publication No. 2009/0009834 to Yaqoob et al., published Jan. 8, 2009.

In addition, the following are hereby incorporated by reference in their entireties as though fully and completely set forth herein: U.S. Pat. No. 6,738,653 to Sfez et al, issued May 18, 2004, and U.S. Patent Application Publication No. 2008/0037367 to Gross et al, published Feb. 14, 2008.

The described embodiments can also be applied to fluorescence imaging which uses a chemical probe (molecules) to obtain biochemical information such as abnormality of the tissue, for example, by setting the focus volume to the point where the fluorescence probe is located. The reproducing step for irradiation thereof may be the same as already described above either based on the first embodiment or second embodiment. By focusing light at the position where the fluorescence probe is located, it may be possible to obtain high contrast images of the target, such as for example a tumor.

There might be an issue regarding the methods that utilize the phase conjugation or optimized the wavefront of incident light to see through a scattering medium or focus light inside a scattering, that is, a movement of scatterers. The technique described above is based on an assumption that the scatterers in the medium do not move throughout the process that includes recording and reconstructing (irradiating) steps. If the position of the scatterers are quite different between the recording (or optimizing) step and the reconstructing step, the phase conjugation or the optimized wavefront (using SLM and optimization algorithm) may not be "optimized irradiation" to focus light in a scattering medium.

Although the movement of the scatterers is issue to focus light, the decay of the optimized wavefront or phase conjugation provides useful information regarding movement of scatterers that might be related to diagnostic information if the scattering medium is a living tissue such as blood flow.

The optimized wavefront can focus on a local volume determined by the confocal system. Therefore, if the irradiation is followed by optical signal measurement, the obtained signal may be maximum just after the optimization or recording process due to the optimized incident light. However, because of the movement of scatterers, the optimized wavefront becomes less and less optimized one as time advances.

Figure 4:
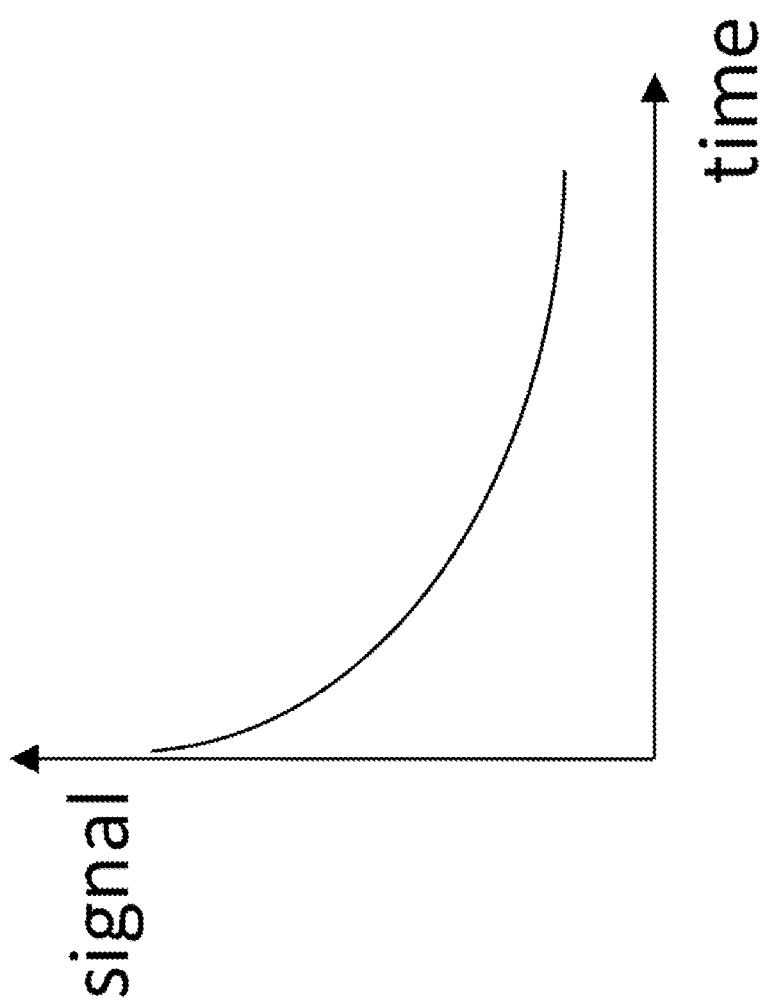
FIG. 4 illustrates a decay of a signal.

As a result, the obtained signal decreases with time as shown in FIG. 4. The signal may be measured as a function of time with optimized wavefront obtained by the optimization of the wavefront. This decay reflects the speed of scatterers in the scattering medium. If the scatterers move very fast, the signal decays very rapidly. On the other hand, if the scatterers move very slow, the signal decays slowly. From this measurement, the information as to the flow of the scatterers may be extracted. Information about the decay of the signal can be displayed on a display to show a user.

The signal described above can be a photoacoustic signal, an acousto-optical signal, or a fluorescent signal (if a chemical probe is used), instead of light signal obtained by the confocal system that utilizes this irradiating method. By monitoring the signal obtained by an imaging system with this irradiation apparatus, this additional information regarding the scattering property of the medium may be obtained. Information about the variation of the signal can be obtained and displayed on a display 297 in FIG. 3.

The focus point can be controlled at a position, which specified by a user, inside a scattering medium by controlling a confocal system including a lens unit and an aperture.

As to the imaging by using the optimized wavefront or the phase conjugate wavefront, the following are hereby incorporated by reference in their entireties as though fully and completely set forth herein: U.S. Pat. No. 5,441,054 to Tsuchiya, issued Aug. 15, 1995, U.S. Pat. No. 5,477,051 to Tsuchiya, issued Dec. 19, 1995, U.S. Pat. No. 5,517,987 to Tsuchiya, issued May 21, 1996, and U.S. Pat. No. 5,424,843 to Tromberg et al, issued Jun. 13, 1995. The following are hereby incorporated by reference in their entireties as though fully and completely set forth herein: U.S. Pat. No. 4,385,634 to Bowen, issued May 31, 1983, U.S. Pat. No. 5,840,023 to Oraevsky et al, issued Nov. 24, 1998, and U.S. Pat. No. 5,713,356 to Kruger, issued Feb. 3, 1998.

While the embodiments according to the present invention have been described with reference to exemplary embodiments, it is to be understood that the present invention is not limited to the above described embodiments. The scope of the following claims is to be accorded the broadest interpretation so as to encompass all such modifications and equivalent structures and functions.

What is claimed is:
1. An apparatus comprising:
a light source configured to emit an electromagnetic wave;
a spatial light modulator configured to modulate a wavefront of the electromagnetic wave to irradiate a sample;
a confocal system including a plate with an aperture and a lens unit configured to set a focal point in the sample;
a photodetector configured to detect a signal corresponding to an electromagnetic wave coming from the focal point of the sample through the confocal system; and a controller configured to control the spatial light modulator to optimize the wavefront of the electromagnetic wave in such a way that the signal detected by the photodetector is enhanced,
wherein the controller is configured to control the light source in such a way that a power of the electromagnetic wave whose wavefront is optimized is different from a power of the electromagnetic wave whose wavefront is not optimized, and
wherein the controller is configured to reconstruct an image using a signal generated in response to the irradiation of an electromagnetic wave whose wavefront is optimized and power is different from the power of the electromagnetic wave whose wavefront is not optimized.

2. The apparatus according to claim 1, wherein the spatial light modulator is a liquid crystal on silicon (LCOS) or a digital micro-mirror device (DMD).

3. The apparatus according to claim 1, wherein the spatial light modulator has a plurality of segments, and the controller controls a phase value of each of the plurality of segments for optimization.

4. The apparatus according to claim 1, wherein the photodetector is a photomultiplier tube.

5. The apparatus according to claim 1, wherein the controller is configured to reconstruct the image using a photoacoustic signal as the signal generated in response to the irradiation of an electromagnetic wave whose wavefront is optimized and power is controlled.

6. The apparatus according to claim 1, wherein the controller is configured to control the spatial light modulator to optimize the wavefront of the electromagnetic wave in such a way that the signal detected by the photodetector is maximized.

7. The apparatus according to claim 1, wherein the controller is configured to control the spatial light modulator to optimize the wavefront of the electromagnetic wave in such a way that the signal detected by the photodetector is load a specified value.

8. The apparatus according to claim 1, wherein the photodetector is configured to detect a signal as a function of time corresponding to an electromagnetic wave of which wavefront is optimized coming from the focal point of the sample through the confocal system, and
wherein the controller is configured to obtain information regarding movement of a medium positioned at the focal point based on the signal as a function of time corresponding to the electromagnetic wave of which wavefront is optimized.

9. The apparatus according to claim 8, wherein the controller is configured to obtain the information regarding a speed of the medium positioned at the focal point as the information regarding movement of the medium positioned at the focal point.

10. The apparatus according to claim 8, wherein the controller is configured to obtain the information regarding blood flow as the information regarding movement of the medium positioned at the focal point.

11. The apparatus according to claim 8, wherein the controller is configured to cause a display to display the information regarding movement of the medium.

12. The apparatus according to claim 1, wherein the controller is configured to obtain the information regarding movement of the medium positioned at the focal point based on a decay of the signal corresponding to the electromagnetic wave of which wavefront is optimized.

13. The apparatus according to claim 1, wherein the controller is configured to cause a display to display the reconstructed image.

14. An apparatus comprising:
a light source configured to emit an electromagnetic wave;
a spatial light modulator configured to modulate a wavefront of the electromagnetic wave to irradiate a sample;
a lens unit configured to set a focal point in the sample;
a plate with an aperture which forms a confocal system with the lens;
a photodetector configured to detect a signal corresponding to an electromagnetic wave coming from the focal point of the sample through the confocal system; and
a controller configured to control the spatial light modulator to optimize the wavefront of the electromagnetic wave in such a way that the signal detected by the photodetector is enhanced,
wherein the controller is configured to reconstruct an image using a photoacoustic signal generated in response to the irradiation of an electromagnetic wave whose wavefront is optimized.

15. The apparatus according to claim 14, wherein the controller is configured to control the spatial light modulator to optimize the wavefront of the electromagnetic wave in such a way that the signal detected by the photodetector is maximized.

16. The apparatus according to claim 14, wherein the controller is configured to control the spatial light modulator to optimize the wavefront of the electromagnetic wave in such a way that the signal detected by the photodetector is load a specified value.

* * * * *